United States Patent [19]

Hebborn et al.

[11] Patent Number: 5,246,439
[45] Date of Patent: Sep. 21, 1993

[54] ELECTROSURGERY EQUIPMENT

[75] Inventors: Kevin A. Hebborn, Hove; Geoffrey P. Taylor, Findon, both of England

[73] Assignee: Smiths Industries Public Limited Company, London, England

[21] Appl. No.: 937,717

[22] Filed: Sep. 1, 1992

[30] Foreign Application Priority Data

Sep. 14, 1991 [GB] United Kingdom ............... 9119695

[51] Int. Cl.$^5$ ............................................. A61B 17/39
[52] U.S. Cl. ........................................ 606/35; 128/908
[58] Field of Search ............................ 606/32, 35, 38; 128/908

[56] References Cited

U.S. PATENT DOCUMENTS

| | | | |
|---|---|---|---|
| 3,897,787 | 8/1975 | Ikuno et al. | 128/303.14 |
| 3,923,063 | 12/1975 | Andrews et al. | 128/303.14 |
| 4,094,320 | 6/1978 | Newton et al. | 606/35 |
| 4,122,854 | 10/1978 | Blackett | 606/35 |
| 4,231,372 | 11/1980 | Newton | 606/35 |
| 4,662,369 | 5/1987 | Ensslin | 606/35 |
| 4,741,334 | 5/1988 | Irnich | 128/303.13 |

FOREIGN PATENT DOCUMENTS

| | | | |
|---|---|---|---|
| 0201103 | 11/1986 | European Pat. Off. | |
| 0332307 | 9/1989 | European Pat. Off. | |
| 2365276 | 7/1974 | Fed. Rep. of Germany | |
| 2821498 | 11/1978 | Fed. Rep. of Germany | 606/38 |
| 855459 | 11/1960 | United Kingdom | |
| 2146534 | 4/1985 | United Kingdom | 606/35 |

Primary Examiner—Lee S. Cohen
Attorney, Agent, or Firm—Pollock, Vande Sande and Priddy

[57] ABSTRACT

Electrosurgery equipment has an alarm circuit for detecting when a return plate electrode is incorrectly attached. Capacitive dividers are connected between ground and each of the power supply line to the active electrode and the power supply return line from the plate electrode. The outputs of the capacitive dividers are supplied to the two inputs of a differential amplifier which provides an output to one input of a comparator. Another input of the capacitor is connected to a reference source. When the output of the differential amplifier rises above the reference source, the comparator produces an alarm signal which inhibits the power supply and gives an audible alarm.

5 Claims, 1 Drawing Sheet

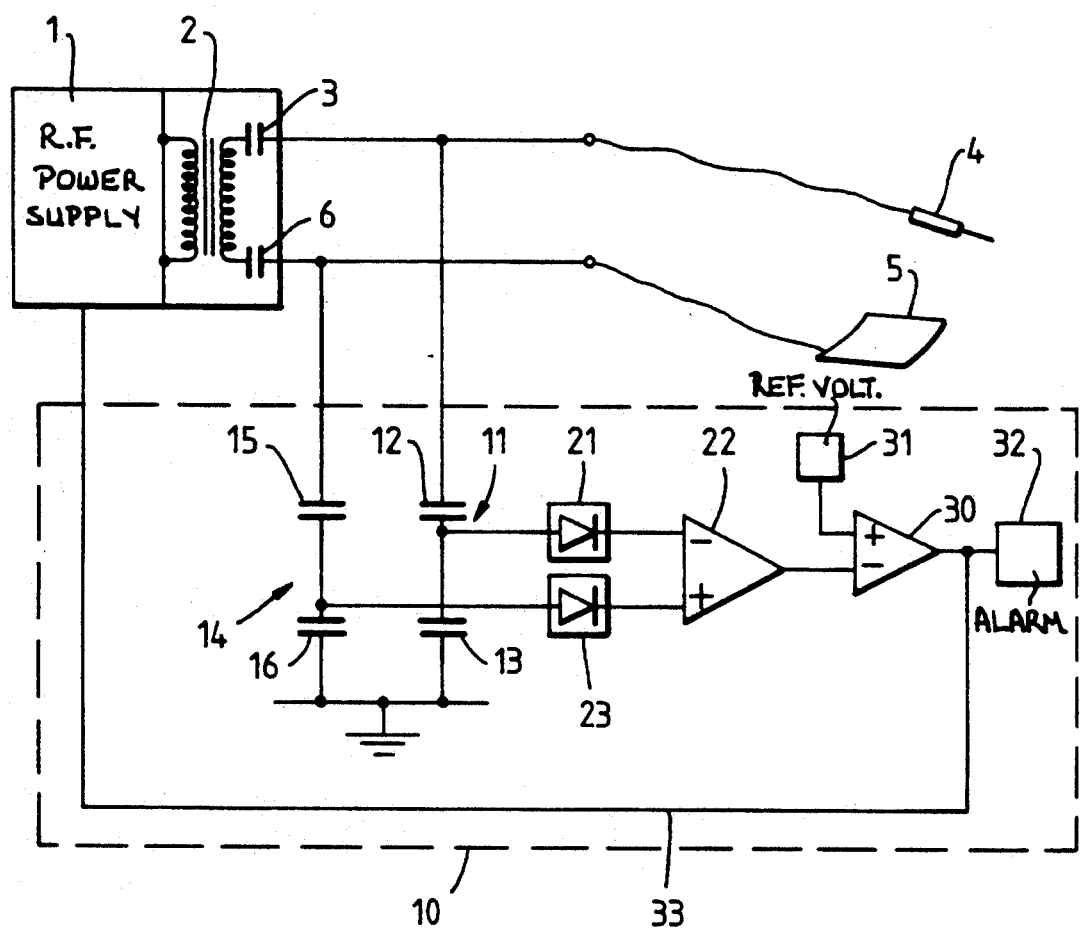

ELECTROSURGERY EQUIPMENT

BACKGROUND OF THE INVENTION

This invention relates to electrosurgery equipment.

Electrosurgery equipment is used to perform cutting or coagulation operations during surgery. Radio frequency current is supplied to an active, hand-held electrode that the surgeon manipulates in order to perform the operation. Current is returned to the electrosurgery generator via a large area plate which is attached to a part of the patient's body. The large area of the return plate ensures that there is a low current density in this region, so that the patient's tissue is not damaged.

One of the problems with electrosurgery equipment of this kind is that the return electrode may separate from the patient so that the contact area is reduced. This can lead to burning of the tissue in the regions where the plate and patient tissue contact. One way of overcoming this problem is to use a return plate electrode that is divided into two parts which are isolated electrically from one another. When the plate is in good contact with the patient's tissue, there will be a low resistance between the two parts of the electrode. By monitoring the resistance between the two parts of the electrode it is possible to detect when the electrode becomes separated from the patient and to cause an alarm or disconnection of the power supply. The problem with this arrangement, however, is that it is necessary to use a special plate electrode.

It is an object of the present invention to provide equipment that does not require a special plate electrode.

BRIEF SUMMARY OF THE INVENTION

According to one aspect of the present invention there is provided electrosurgery equipment including an r.f. power supply arranged to supply power to an active electrode and having a return path via a large area plate electrode, means for measuring the difference between the voltage on the active electrode with respect to ground and the plate electrode with respect to ground, and means for providing an alarm signal when the voltage on the plate electrode rises relative to the active electrode by more than a predetermined amount with respect to ground.

The alarm signal may be provided to inhibit the output from the power supply. The voltage difference measuring means may include a first capacitive divider connected between the active electrode and ground and a second capacitive divider connected between the plate electrode and ground. The equipment may include a differential amplifier having one input connected with the first capacitive divider and another input connected with the second capacitive divider. The equipment may include a comparator that receives at one input the output of the differential amplifier and at another input a reference signal, the comparator being arranged to provide the alarm signal when the output of the differential amplifier rises above the reference signal.

Electrosurgery equipment in accordance with the present invention will now be described, by way of example, with reference to the accompanying drawing.

BRIEF DESCRIPTION OF THE DRAWING

The drawing shows the equipment schematically.

DETAILED DESCRIPTION OF PREFERRED EMBODIMENT

The electrosurgery equipment includes a conventional r.f. power supply 1 which provides an r.f. output via a transformer 2 and a capacitor 3 to an active, hand-held electrode 4. Return current from the patient is supplied via a large area flexible plate electrode 5 which is secured firmly to a part of the patient. The return current is supplied back to the transformer 2 via a second capacitor 6.

The equipment also includes an alarm circuit 10 which monitors correct attachment of the return plate 5 to the patient. The alarm circuit 10 includes a first capacitive divider 11 comprising a series connection of two capacitors 12 and 13 connected at one end to the supply line to the active electrode 4 and at the other end to ground. A second capacitive divider 14 comprising a series connection of two capacitors 15 and 16 is connected at one end to the return line from the plate 5 and at the other end to ground. The a.c. voltage at a point between the two capacitors 12 and 13 in the first divider 11 is rectified by a rectifier circuit 21 to produce a d.c. voltage which is applied to one input of a differential amplifier 22. Similarly, the a.c. voltage at a point between the capacitors 15 and 16 in the second divider 14 is rectified by a rectifier circuit 23 to produce a d.c. voltage which is applied to the other input of the differential amplifier 22. The differential amplifier 22 amplifies the difference between the two d.c. voltages. The output of the differential amplifier 22 is connected to one input of a comparator 30 which receives a reference voltage at its other input from a voltage source 31. The output from the comparator 30 is connected to an audible alarm 32 and to the power supply 1 via line 33.

When the plate 5 is properly attached to the patient, the patient's body provides a capacitance between the plate and ground of the order of hundreds of picofarads. This causes the a.c. voltage between the plate 5 and ground to remain low.

If the plate 5 becomes detached, or the active electrode 4 is grounded, the a.c. voltage on the plate with respect to ground will rise relative to the voltage on the active electrode.

The rectifier circuits 21 and 23 and the gain of the differential amplifier 22 are arranged such that, when the plate 5 is properly attached to the patient and the active electrode 4 is not grounded, the output from the differential amplifier is below the reference voltage. When, however, the plate 5 becomes detached, or the active electrode 4 becomes grounded, the output from the differential amplifier 22 rises above the reference level and causes the comparator 30 to generate an alarm signal.

The alarm signal is supplied both to the audible alarm 32, to provide a sound that alerts the surgeon, and to the power supply 1 to disable the output and terminate the supply of current to the patient, thereby reducing the risk of burns to the patient.

It will be appreciated that the equipment need not employ capacitive dividers but could have alternative means for measuring the difference between the voltages on the active electrode and plate electrode.

It can be seen that present invention enables an alarm signal to be produced without the need to use special electrodes.

What we claim is:

1. Electrosurgery equipment comprising: an r.f. power supply; an active electrode; a power supply line between the power supply and the active electrode; a large area plate electrode; a return path between the plate electrode and the power supply; an alarm circuit having first and second inputs; means connecting the first input of the alarm circuit between the active electrode and ground; means connecting the second input of the alarm circuit between the plate electrode and ground, the alarm circuit including a comparator operable to determine when the voltage on the plate electrode rises relative to the voltage on the active electrode by more than a predetermined amount with respect to ground, and the alarm circuit including means for providing an alarm signal in accordance therewith.

2. Electrosurgery equipment according to claim 1, wherein the equipment includes a connection between the alarm circuit and the power supply, and wherein the alarm signal is supplied via said connection to means operable to inhibit an output from the power supply.

3. Electrosurgery equipment according to claim 1 wherein the alarm circuit includes a first capacitive divider connected between the active electrode and ground, and a second capacitive divider connected between the plate electrode and ground, said means for providing an alarm signal being connected with the first and second capacitive dividers.

4. Electrosurgery equipment according to claim 3, wherein said means connected with said dividers includes a differential amplifier having two inputs, means connecting one input of the differential amplifier with the first capacitive divider and means connecting the other input of the differential amplifier with the second capacitive divider such that the differential amplifier provides an output in accordance with the difference in voltage on the two dividers.

5. Electrosurgery equipment according to claim 4, including a source of a reference signal, means connecting the comparator to both the output of the differential amplifier and the reference signal source so that the comparator provides said alarm signal when the output of the differential amplifier rises above the reference signal.

* * * * *